United States Patent
Tincher

(10) Patent No.: US 10,843,152 B2
(45) Date of Patent: Nov. 24, 2020

(54) OUT-OF-PRODUCT DETECTION USING OPTICAL SENSORS

(71) Applicant: Delaware Capital Formation, Inc., Wilmington, DE (US)

(72) Inventor: Terry Tincher, Lebanon, OH (US)

(73) Assignee: Delaware Capital Formation, Inc., Wilmington, DE (US)

( * ) Notice: Subject to any disclaimer, the term of this patent is extended or adjusted under 35 U.S.C. 154(b) by 453 days.

(21) Appl. No.: 15/689,255

(22) Filed: Aug. 29, 2017

(65) Prior Publication Data
US 2019/0060857 A1 Feb. 28, 2019

(51) Int. Cl.
| | |
|---|---|
| G01F 23/00 | (2006.01) |
| B01F 15/04 | (2006.01) |
| A47L 15/00 | (2006.01) |
| A47L 15/44 | (2006.01) |
| G01N 21/05 | (2006.01) |
| B01F 1/00 | (2006.01) |
| G01N 30/74 | (2006.01) |
| A61M 5/168 | (2006.01) |
| G01F 23/292 | (2006.01) |

(52) U.S. Cl.
CPC ...... *B01F 15/0408* (2013.01); *A47L 15/0055* (2013.01); *A47L 15/4436* (2013.01); *A61M 5/1684* (2013.01); *B01F 1/0027* (2013.01); *G01F 23/292* (2013.01); *G01F 23/2921* (2013.01); *G01N 21/05* (2013.01); *G01N 30/74* (2013.01)

(58) Field of Classification Search
CPC .......... B01F 15/0408; B01F 1/0027; A47L 15/0055; A47L 15/4436; A61M 5/1684; G01F 23/292; G01F 23/2921; G01N 21/05; G01N 30/74

USPC .................................................... 702/189, 50
See application file for complete search history.

(56) References Cited

U.S. PATENT DOCUMENTS

| | | | |
|---|---|---|---|
| 4,964,185 A | 10/1990 | Lehn | |
| 5,636,017 A | 6/1997 | Bruno et al. | |

(Continued)

FOREIGN PATENT DOCUMENTS

| | | |
|---|---|---|
| KR | 20100078696 A | 7/2010 |
| WO | 2008142922 A1 | 11/2008 |

OTHER PUBLICATIONS

European Patent Office, European Search Report in EP 18186691, dated Jan. 7, 2019.

*Primary Examiner* — Michael P Nghiem
(74) *Attorney, Agent, or Firm* — Wood Herron & Evans LLP

(57) ABSTRACT

Systems, methods, and software program products for detecting an out-of-product condition in a chemical dispensing system. An optical sensor includes a photodetector and a light source configured to generate a beam of light. The light source is positioned such that the beam of light is incident on a supply line at an oblique angle. The supply line displaces the beam of light in dependence on the refractive index of a medium in the supply line. The photodetector is positioned so that it is in the optical path of the displaced beam of light when the refractive index of the of the medium in the supply line is indicative of one of a wet state or a dry state. A detection module receives an electrical signal from the photodetector and determines if the out-of-product conditions exists base thereon.

7 Claims, 10 Drawing Sheets

(56) References Cited

U.S. PATENT DOCUMENTS

| | | | |
|---|---|---|---|
| 6,111,263 | A | 8/2000 | Wahlberg |
| 7,924,424 | B2 | 4/2011 | Erickson et al. |
| 8,004,683 | B2 | 8/2011 | Tokhtuev et al. |
| 9,095,248 | B2 | 8/2015 | Fisher |
| 9,282,875 | B2 | 3/2016 | Fisher |
| 10,591,411 | B1* | 3/2020 | Tincher .............. G01N 21/3151 |
| 2009/0097029 | A1* | 4/2009 | Tokhtuev ............ A61M 5/1684 |
| | | | 356/409 |
| 2009/0262351 | A1 | 10/2009 | Erickson et al. |
| 2019/0079543 | A1* | 3/2019 | Tincher .................. B01F 5/043 |
| 2020/0080884 | A1* | 3/2020 | Tincher ............... G01F 23/2921 |

* cited by examiner

OUT-OF-PRODUCT DETECTION USING OPTICAL SENSORS

BACKGROUND

The invention generally relates chemical dispensing systems for laundry, ware-wash, and healthcare applications, and in particular, to systems, methods, and software products for detecting an out-of-product condition in a chemical dispensing system.

The dispensing of liquid chemical products from one or more chemical receptacles is a common requirement of many industries. For example, in an industrial laundry facility, each of several washing machines must be provided with aqueous solutions containing various quantities of alkaloid, detergent, bleach, starch, softener, and/or other chemical products.

The chemical products being dispensed are typically stored in containers with probe assemblies that monitor the level of products in the containers. Probe assemblies may detect the level of products in the containers using mechanical floats or electrical probes, for example. One type of probe assembly includes two probes separated by a distance so that the probe assembly has a high input impendence when exposed to air. Because the products are typically conductive, the input impendence of this type of probe assembly is lower when the probes are in contact with the product. To provide an indication of the level of product in a container, the probe assembly is mounted in the container so that the probes are in contact with the product, or the float causes a switch to be in a particular state (e.g., open or closed) when the container is sufficiently full. When the level of product drops below the probes, the electrical probes are exposed to air, increasing the input impedance of the probe assembly, or the float drops sufficiently to change the state of the switch. To notify the operator of the chemical dispensing system that the container is running low on product, a monitoring device is connected to the probe assembly. In this type of detection system, the monitoring device is configured to detect the increase in the input impedance of the probe assembly or the change in the state of the switch, and may thereby notify an operator that the product is about to run out by providing an alarm.

Because these level monitoring systems rely on the measured input impedance of the probe assembly to detect the level of the product, anything that affects this measurement can have a negative impact on the reliability of the system. Likewise, the buildup of deposits on the float mechanism can impair the ability of the float to accurately detect the level of the product. Probe assemblies may experience reliability issues over time from the product attacking the probes due to the corrosive nature of many of the chemicals typically found in the product. Fouled or otherwise compromised probe assemblies and/or monitoring devices may cause erroneous readings. These erroneous readings may result in false alarms and/or failures to notify the operator that a product is running out. In addition, even if the level detection system is functioning correctly, pumps or other components that deliver the product may malfunction, thereby causing the chemical delivery system to fail to deliver product.

To ensure products are being delivered to the machines fed by the chemical dispensing system, systems have been developed that monitor the flow of product to the machines. However, these systems typically rely on electrical sensors subject to the same failures as the level monitoring systems discussed above. Unreliable monitoring systems may result in the machines attached to the chemical dispensing system running without the required amounts of the chemical products being dispensed. The performance of the machines fed by the chemical dispensing system may be adversely affected due to too little of the product being dispensed, reducing the quality of machine's output and increasing expenses by requiring goods to be re-processed through the affected machine.

Therefore, there is a need for improved systems, methods, and software products for monitoring the delivery of chemical products in chemical dispensing systems.

SUMMARY

In an embodiment of the invention, an apparatus for monitoring a chemical dispensing system is provided. The apparatus includes a photodetector, a light source configured to generate a beam of light, and a holder. The holder is configured to locate the light source and the photodetector relative to a tube that carries a product such that the beam of light has an oblique angle of incidence with respect to an outer surface of the tube, and the photodetector is in an optical path of the beam of light when the tube is in one of a dry state or a wet state and is not in the optical path of the beam of light when the tube is in the other of the dry state or the wet state.

In another embodiment of the invention, a method of monitoring the chemical dispensing system is provided. The method includes directing the beam of light at the point of incidence on the outer surface of the tube so that the beam of light has the oblique angle of incidence with respect to the outer surface of the tube. The method further includes receiving the beam of light at the photodetector after the beam of light has passed through the tube, and determining the tube is in one of the wet state or the dry state based on an electrical signal output by the photodetector.

In another embodiment of the invention, a computer program product for monitoring the chemical dispensing system is provided. The computer program product includes a non-transitory computer-readable storage medium, and program code stored on the non-transitory computer-readable storage medium. The program code is configured to, when executed by one or more processors, cause the one or more processors to cause the beam of light to be directed at the point of incidence on the outer surface of the tube, the beam of light having the oblique angle of incidence with respect to the outer surface of the tube. The program code is further configured to cause the one or more processors to receive the signal from the photodetector configured to receive the beam of light after the beam of light has passed through the tube if the tube is in one of the wet state or the dry state, and determine the tube is in one of the wet state or the dry state based on the signal received from the photodetector.

The above summary may present a simplified overview of some embodiments of the invention to provide a basic understanding of certain aspects the invention discussed herein. The summary is not intended to provide an extensive overview of the invention, nor is it intended to identify any key or critical elements, or delineate the scope of the invention. The sole purpose of the summary is merely to present some concepts in a simplified form as an introduction to the detailed description presented below.

BRIEF DESCRIPTION OF THE DRAWINGS

The accompanying drawings, which are incorporated in and constitute a part of this specification, illustrate various embodiments of the invention and, together with the general description of the invention given above, and the detailed description of the embodiments given below, serve to explain the embodiments of the invention.

DETAILED DESCRIPTION

Figure 1:
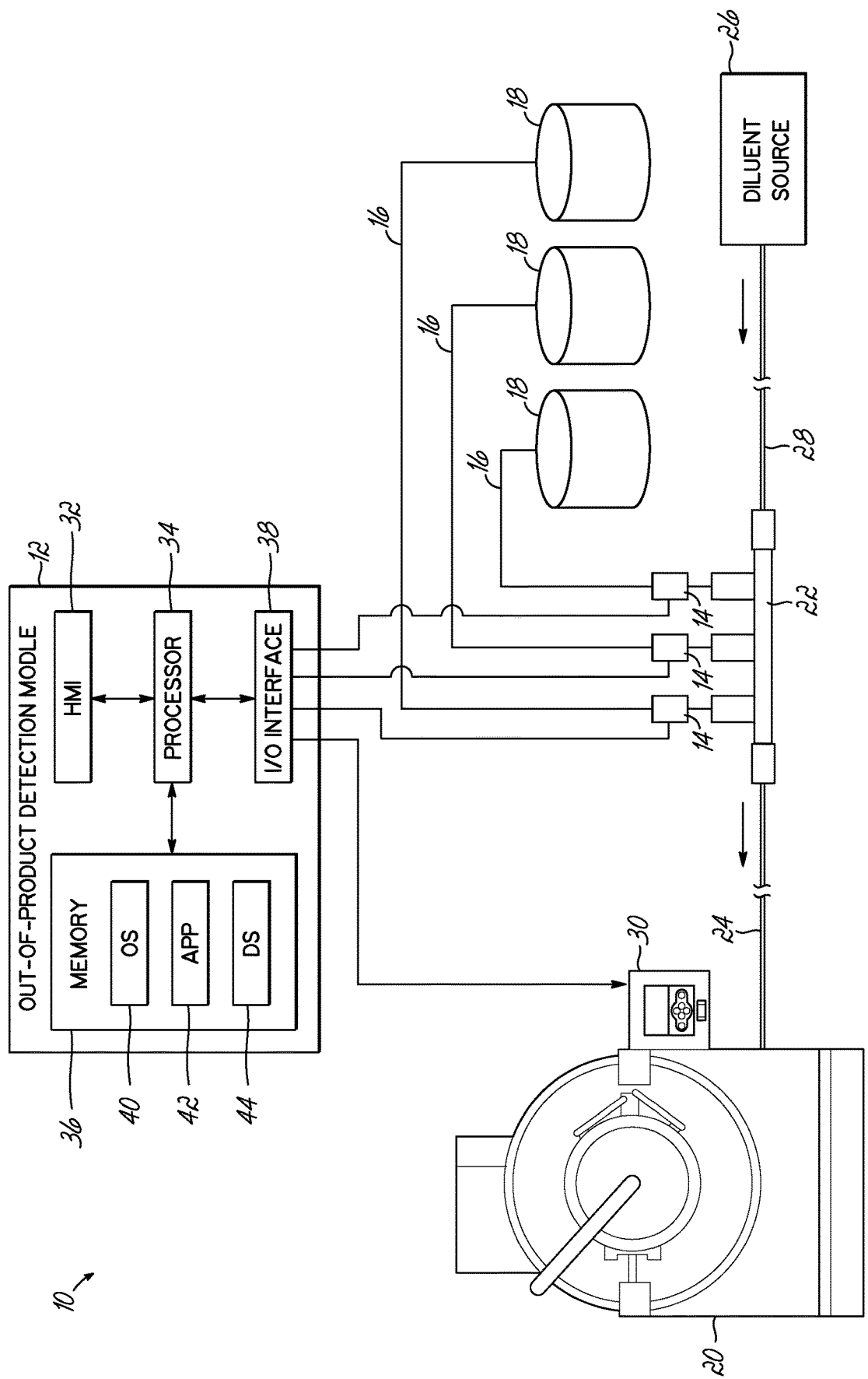
FIG. 1 is a diagrammatic view of an operating environment including an out-of-product detection module, and an optical sensor that monitors a supply line which supplies product to a machine.

FIG. 1 depicts an operating environment for a chemical dispensing system 10 that includes an Out-Of-Product (OOP) detection module 12 in communication with one or more (e.g., three) optical sensors 14. Each of the optical sensors 14 may be coupled to a supply line 16 that fluidically couples a source of product 18 to a machine 20, such as a washing machine. Each supply line 16 may comprise a tube of optically transparent material having an index of refraction n greater than that of air (e.g., of about 1.52), and may couple the sources of products 18 to the machine 20, such as via a flush manifold 22. Examples of tubing suitable for use in the product supply lines may include Tygon® tubing, which is available from Saint-Gobain S.A. of Courbevoie, France. For embodiments including the flush manifold 22, an output of the flush manifold 22 may be coupled to the machine 20 by a machine supply line 24, and an input of the flush manifold 22 may be coupled to a source of diluent 26, such as water, by a diluent supply line 28. Each source 18, 26 may selectively provide its product and/or diluent to the machine 20 in response to signals from a controller 30. The controller 30 may thereby control the amount and timing of product and/or diluent provided to the machine 20 by regulating the flow of the products and diluent through the flush manifold 22.

The detection module 12 may include a Human Machine Interface (HMI) 32, a processor 34, a memory 36, and an input/output (I/O) interface 38. The HMI 32 may include output devices, such as an alphanumeric display, a touch screen, and/or other visual and/or audible indicators that provide information from the processor 34 to a user. The HMI 32 may also include input devices and controls, such as an alphanumeric keyboard, a pointing device, keypads, pushbuttons, control knobs, etc., capable of accepting commands or input from the user and transmitting the entered input to the processor 34. By way of example, the input and output devices of HMI 32 may include a membrane overlay with embedded Light Emitting Diodes (LEDs) and buttons.

The processor 34 may include one or more devices configured to manipulate signals (analog or digital) based on operational instructions that are stored in memory 36. Memory 36 may be a single memory device or a plurality of memory devices including but not limited to read-only memory (ROM), random access memory (RAM), volatile memory, non-volatile memory, static random access memory (SRAM), dynamic random access memory (DRAM), flash memory, cache memory, or any other device capable of storing information. Memory 36 may also include a mass storage device (not shown), such as a hard drive, optical drive, tape drive, non-volatile solid state device or any other device capable of storing digital information.

Processor 34 may operate under the control of an operating system 40 that resides in memory 36. The operating system 40 may manage detection module resources so that computer program code embodied as one or more computer software applications 42 residing in memory 36 may have instructions executed by the processor 34. In an alternative embodiment, the processor 34 may execute the applications 42 directly, in which case the operating system 40 may be omitted. One or more data structures 44 may also reside in memory 36, and may be used by the processor 34, operating system 40, and/or application 42 to store data.

The I/O interface 38 operatively couples the processor 34 to other components in the dispensing system 10, such as the optical sensors 14 and/or controller 30. The I/O interface 38 may include signal processing circuits that condition incoming and outgoing signals so that the signals are compatible with both the processor 34 and the components to which the processor 34 is coupled. To this end, the I/O interface 38 may include analog to digital (A/D) and/or digital to analog (D/A) converters, voltage level and/or frequency shifting circuits, optical isolation and/or driver circuits, and/or any other analog or digital circuitry suitable for coupling the processor 34 to the other components of the dispensing system 10. In particular, the I/O interface 38 may include a multiplexer that selectively couples individual optical sensors 14 to the processor 34. Selective coupling may include sequentially coupling each of one or more active detector inputs of the I/O interface 38 to the processor 34 so that the processor 34 can receive electrical signals from and/or provide electrical signals to the optical sensors 14. This feature may enable the processor 34 to selectively activate and/or monitor a plurality of optical sensors 14 using a single input/output port and/or A/D converter. The I/O interface 38 may also include one or more amplifiers that amplify voltages provided by the optical sensors 14 to a level suitable for use by the A/D converter.

Figure 2A:
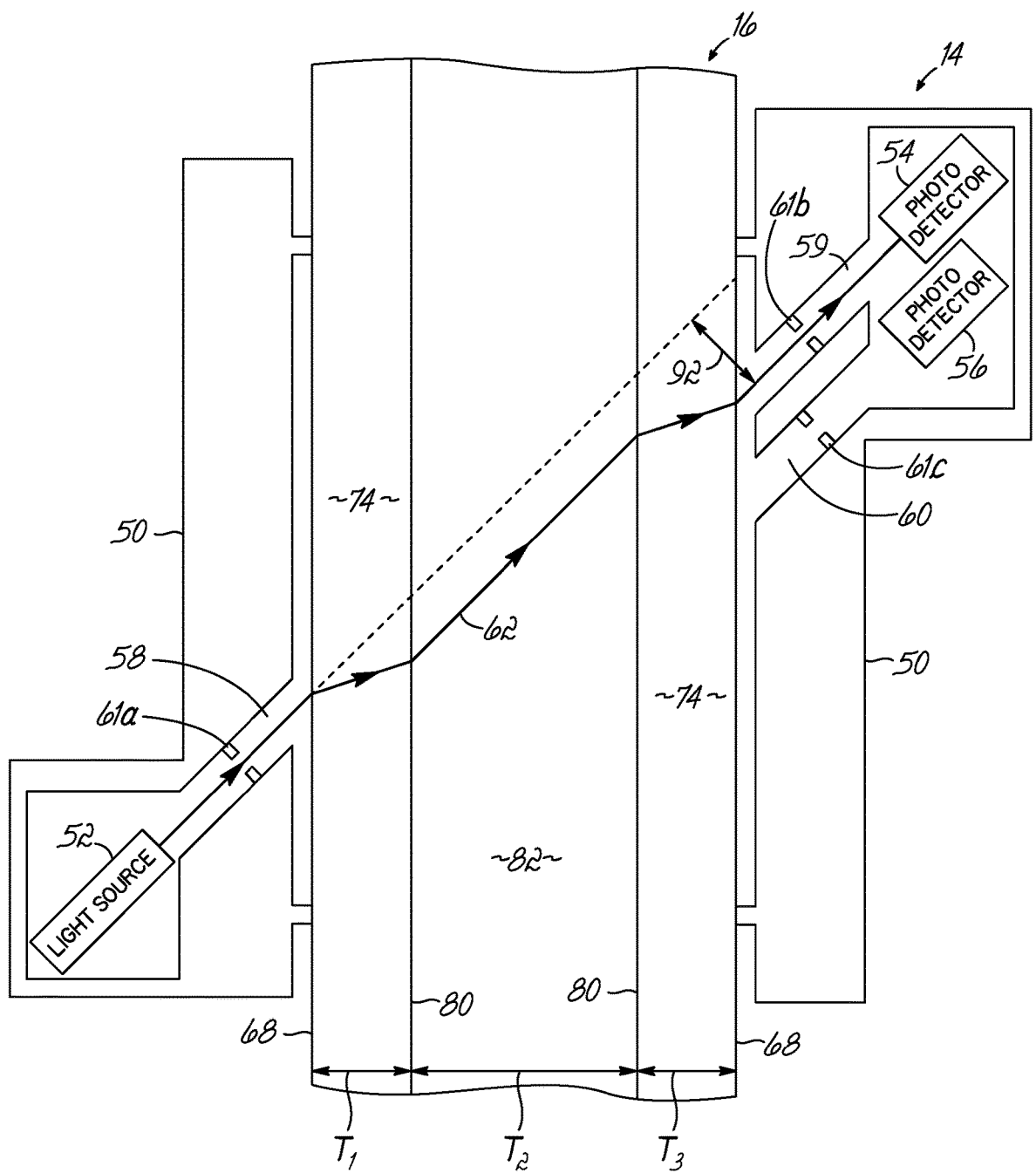
FIG. 2A is a diagrammatic view of an exemplary optical sensor of FIG. 1 including a supply line in a dry state.
Figure 2B:
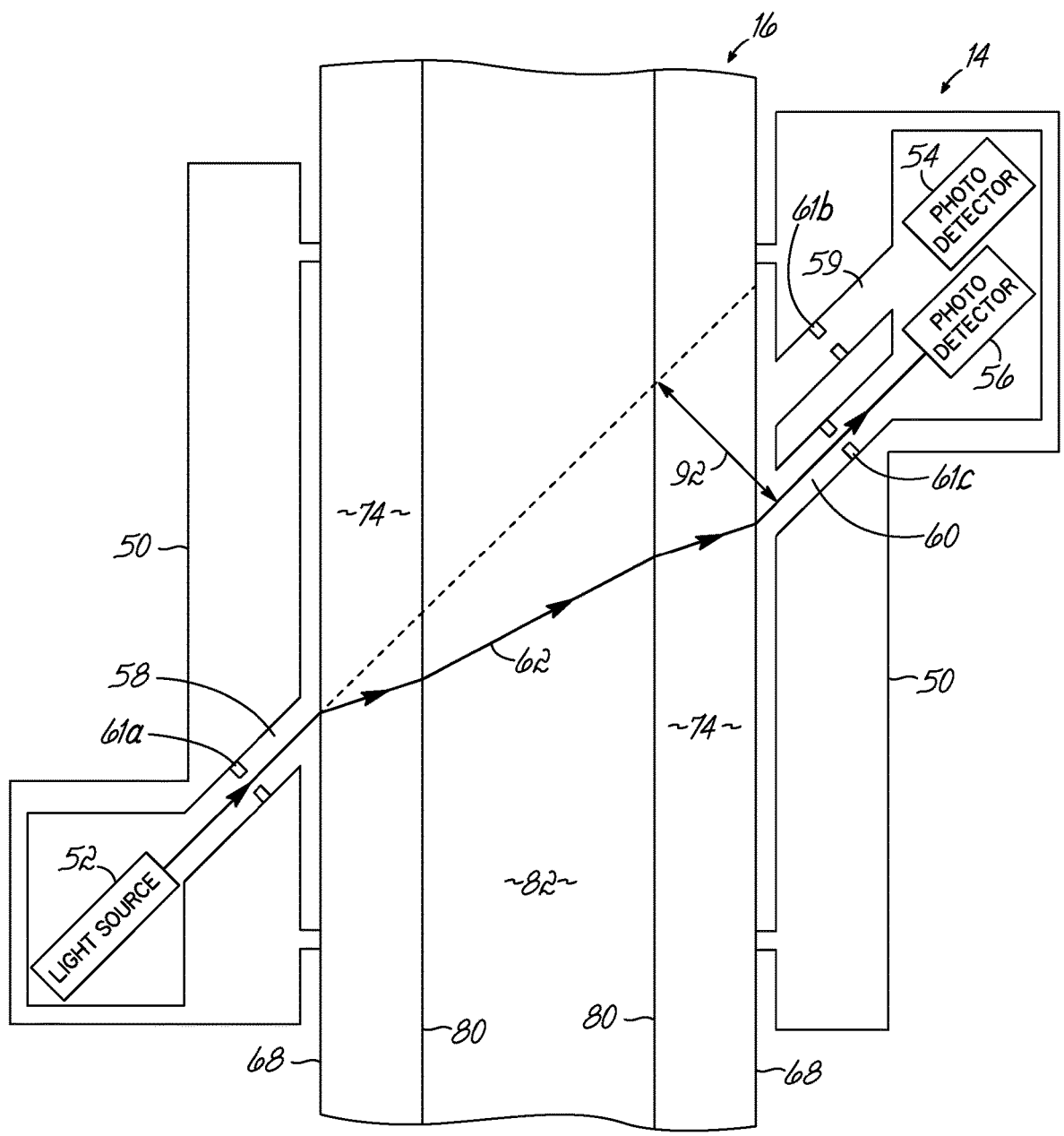
FIG. 2B is a diagrammatic view of an exemplary optical sensor of FIG. 2A showing the supply line in a wet state.

FIGS. 2A and 2B depict an optical sensor 14 in accordance with an embodiment of the invention that includes a holder 50, a light source 52, and one or more (e.g., two) photodetectors 54, 56. The holder 50 may be configured to locate the light source 52 and photodetectors 54, 56 in a fixed position relative to the supply line 16. The holder 50 may include one or more channels 58-60 that provide one or more optical paths for a beam of light 62 emitted by the light source 52. Each of the channels 58-60 coupling the light source 52 and photodetectors 54, 56 to the supply line 16 may include an aperture 61a-61c that defines an opening having a predetermined size and shape. For example, the source channel 58 may include a circular aperture 61a having a diameter of 2 mm or less, and the photodetector channels 59, 60 may each include a circular aperture 61b, 61c having a diameter of 3 mm or less. The apertures 61a-61c may be defined by baffles formed in the channel 58-60 as depicted in FIGS. 2A and 2B, or by the diameter of the channel 58-60 itself. The apertures 61a-61c may be configured to allow the beam of light 62 to reach one or the other of the photodetectors 54, 56 when the medium 82 in supply line 16 has a refractive index n specific to that photodetector (e.g., n=1.3 or 1.0), and may shield the photodetectors 54, 56 from the beam of light 62 when the medium 82 in the supply line has a different refractive index.

Figure 3:
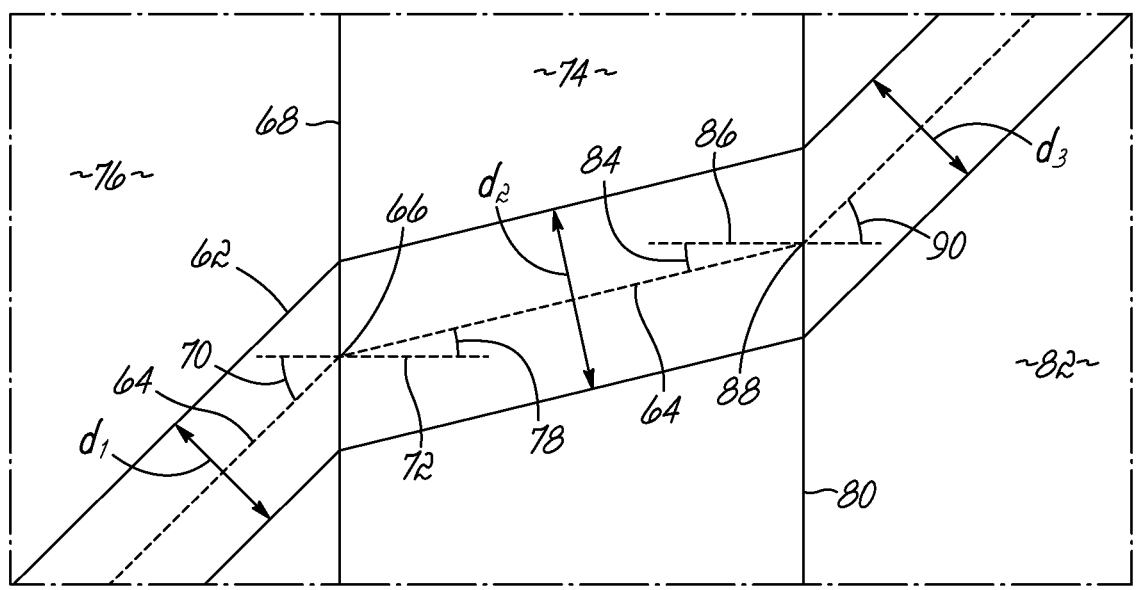
FIG. 3 is a diagrammatic view of a portion of the supply line in FIG. 2A showing refraction of a beam of light passing through the supply line.

Referring now to FIG. 3, and with continued reference to FIGS. 2A and 2B, the light source 52 may be positioned by the holder 50 so that a centerline 64 of beam of light 62 is centered on a point of incidence 66 on an outer surface 68 of supply line 16. The beam of light 62 may have an angle of incidence 70 relative to a line 72 normal to the outer surface 68 at the point of incidence 66. The angle of incidence 70 may be an oblique angle (e.g., 45 to 70 degrees). For a supply line 16 comprised of a medium 74 having an index of refraction different than the medium 76 through which the beam of light 62 passes before encountering the outer surface 68, the beam of light 62 is refracted so that it assumes an angle of emittance 78 relative to line 72.

The relationship between the angle of incidence 70 and the angle of emittance 78 is governed by Snell's law:

$$\frac{n_1}{n_2} = \frac{\sin(\theta_2)}{\sin(\theta_1)} \qquad \text{Eqn. 1}$$

where $n_1$ is the refractive index of the medium 76 external to the supply line 16, $n_2$ is the refractive index of the medium 74 of supply line 16, $\theta_1$ is the angle of incidence 70, and $\theta_2$ is the angle of emittance 78. Solving equation 1 for the angle of emittance 78 yields:

$$\theta_2 = \arcsin\left(\frac{n_1 \times \sin(\theta_1)}{n_2}\right) \qquad \text{Eqn. 2}$$

A similar effect may be observed as the beam of light 62 crosses the inner surface 80 of supply line 16 and encounters the medium 82 in supply line 16. The transition from the medium 74 of supply line 16 to the medium 82 in supply line 16 may be determined by Equation 3:

$$\theta_4 = \arcsin\left(\frac{n_2 \times \sin(\theta_3)}{n_3}\right) \qquad \text{Eqn. 3}$$

where $n_3$ is the refractive index of the medium 82 in supply line 16, $\theta_3$ is an angle of incidence 84 relative to a line 86 normal to the inner surface 80 of supply line 16 at a point of incidence 88, and $\theta_4$ is the angle of emittance 90 of the beam of light 62. For embodiments in which the line 86 normal to inner surface 80 is parallel to the line 72 normal to outer surface 68, and the refractive indexes of the media 76, 82 are equal, the angle of incidence 84 may be equal to the angle of emittance 78.

When the beam of light 62 crosses the boundary between mediums (e.g., the boundary between air and a polymer) defined by outer surface 68, the velocity of the beam of light 62 may be altered (e.g., reduced). This change in velocity may cause the beam of light 62 to be refracted towards (in the case of a reduction in velocity) or away (in the case of an increase in velocity) from the line 72 normal to surface 68 at an angle based on the refractive indices of the mediums 74, 76. Indeed, the path of the beam of light 62 may be altered each time it encounters a boundary between any of the medium 76 external to supply line 16, the medium 74 of supply line 16, and the medium 82 in supply line 16. This bending may produce a total lateral shift 92 in the beam of light 62 that is dependent in part on the index of refraction $n_3$ of the medium 82 in the supply line 16. The total lateral shift 92 may be the sum of each lateral shift the beam of light 62 experiences as it propagates from the light source 52 to the photodetectors 54, 56. The total lateral shift 92 introduced over the optical path of beam of light 62 may be determined using Equation 4:

$$L_S = \Sigma T_m \times \sec(\theta_r) \times \sin(\theta_i - \theta_r) \qquad \text{Eqn. 4}$$

where $L_S$ is the total lateral shift, $T_m$ is a thickness (e.g., $T_1$, $T_2$, $T_3$) of each layer of medium (e.g., mediums 74, 76, 82) through which the beam of light 62 passes, $\theta_i$ is the angle of incidence at each respective boundary, and $\theta_r$ is the angle of refraction at each respective boundary.

The energy level of the beam of light 62 may be altered as it propagates over the optical path due to the optical properties of the various media. For example, a certain amount of light may be lost at each boundary due to reflection and diffusion. A lateral dimension d of the beam of light 62 (e.g., $d_1$, $d_2$, $d_3$) may also be altered due to refraction at each boundary. For example, the cross-sectional area of the beam of light 62 may increase or decrease in one dimension. This expansion or contraction of the dimension d may be determined using Equation 5:

$$\frac{d_r}{d_i} = \frac{\cos(\theta_r)}{\cos(\theta_i)} \qquad \text{Eqn. 5}$$

where $d_i$ is the dimension of the incident beam, and $d_r$ is the dimension of the refracted beam.

A portion of the beam of light 62 may also be reflected at each boundary, thereby reducing the power of the refracted beam. To satisfy the law of conservation of energy, the total power of the refracted and reflected portions of the beam must equal the power of the incident beam. The power of the refracted beam as a fraction of the incident power, or transmittance T, is provided by Equation 6:

$$T = \frac{n_r \times \cos(\theta_r) \times |E_r|^2}{n_i \times \cos(\theta_i) \times |E_i|^2} = \frac{n_r \times \cos(\theta_r)}{n_i \times \cos(\theta_i)} \times |t|^2 \qquad \text{Eqn. 6}$$

where $E_r$ is the amplitude of the electric field of the refracted beam of light, $E_i$ is the amplitude of the incident beam of light, $n_r$ is the refractive index of the medium in which the refracted beam of light is propagating, $n_i$ is the refractive index of the medium in which the incident beam of light is propagating, and t is a coefficient equal to the ratio of the amplitude of the electric field of the transmitted beam of light to the amplitude of the electric field of the incident beam of light.

The detection module 12 and/or optical sensors 14 may be configured to determine the presence or absence of product in the supply lines 16 based on these refraction ratios and the lateral shifts 92 produced by interaction of the different indexes of refraction with the beam of light 62. The holder 50 of optical sensor 14 may be configured to position the light source 52 and/or photodetectors 54, 56 so that the amount of energy transferred from the light source 52 through the various media 74, 76, 82 is optimized for reliable detection in view of the angles of refraction and the widening or narrowing of the beam of light 62 across the optical path. This optimization may provide the detection module 12 with a robust signal that enables the module to accurately determine the presence or absence of product in the supply line 16. This signal may be, for example, a voltage output by one or more of the photodetectors 54, 56 indicative of the presence, absence, and/or intensity of the beam of light 62 at the respective photodetector 54, 56.

Although the exemplary optical sensor 14 depicted by FIGS. 2A and 2B includes two photodetectors 54, 56, embodiments of the invention may include optical sensors 14 that have a single photodetector, or more than two photodetectors. Optical sensors 14 may be configured so that the presence of product in the monitored supply line 16 causes the beam of light 62 to be directed to a photodetector (in which case the presence of light at the photodetector would indicate the presence of product in the supply line 16), or away from a photodetector (in which case the presence of light at the photodetector would indicate an absence of product in the supply line 16). Multiple photodetectors in different locations may also be used to determine a type of product in the supply line 16 based on the lateral shift 92 of beam of light 62 caused by differences in the refractive indexes of different products.

The light source 52 may be configured to emit a wavelength of between 900 and 1100 nm, although other wavelengths may also be used. A suitable device that may be used as the light source may be an LED that emits Infrared (IR) light having a wavelength of about 940 nm, for example. The wavelength of the light source 52 may be selected to be one for which the supply line 16 has a high transmittance. For example, it has been determined that model 2735 type of Tygon® tubing has good transmissivity at wavelengths greater than 900 nm with little absorbance of energy.

Figure 4A:
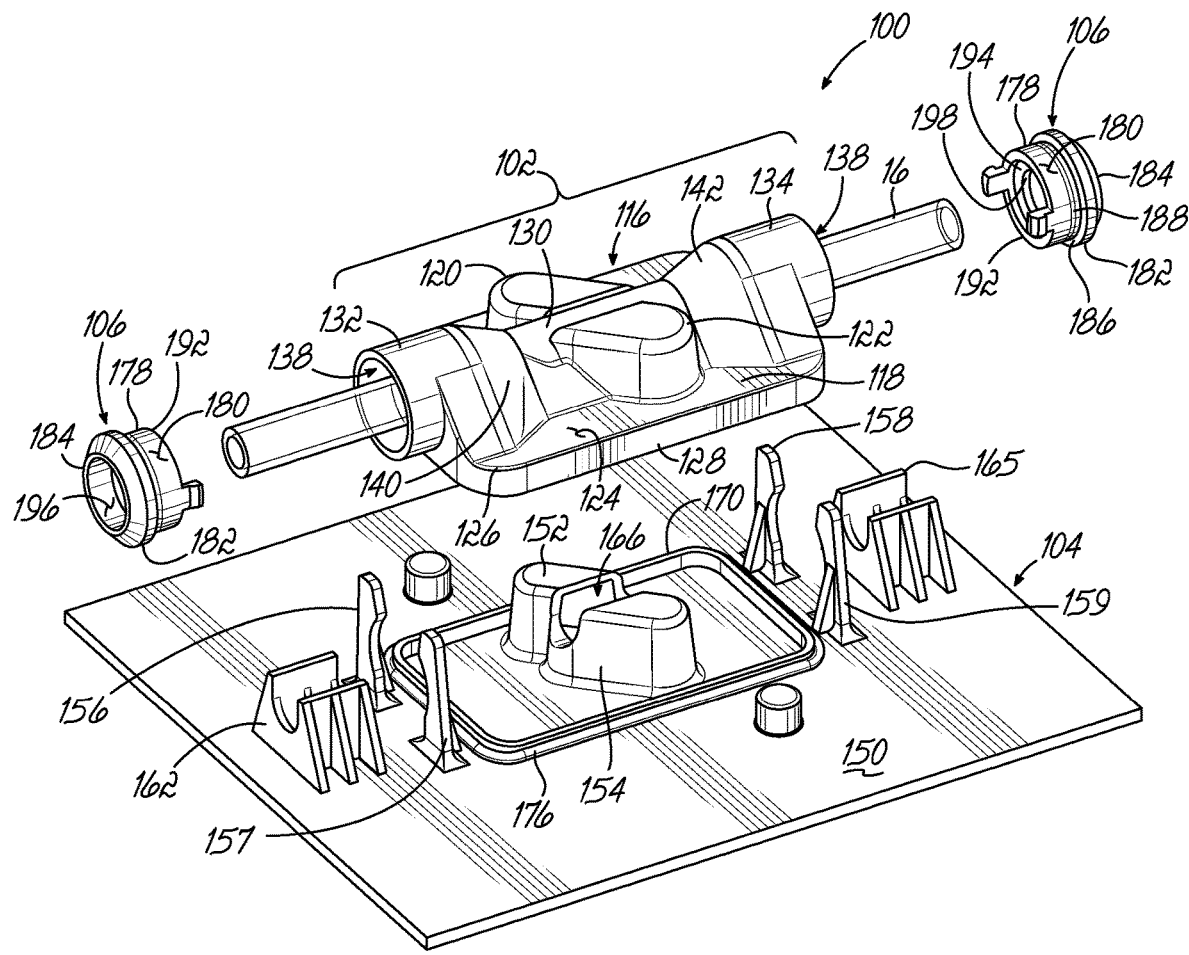
FIG. 4A is an exploded perspective view of an optical sensor assembly in accordance with an embodiment of the invention.
Figure 4A:
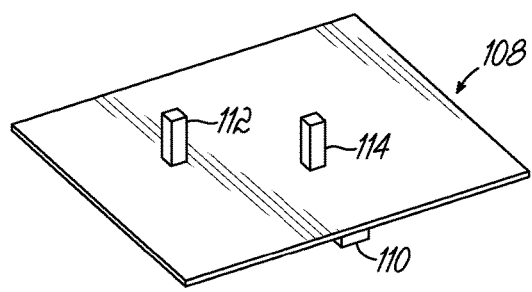
Figure 4B:
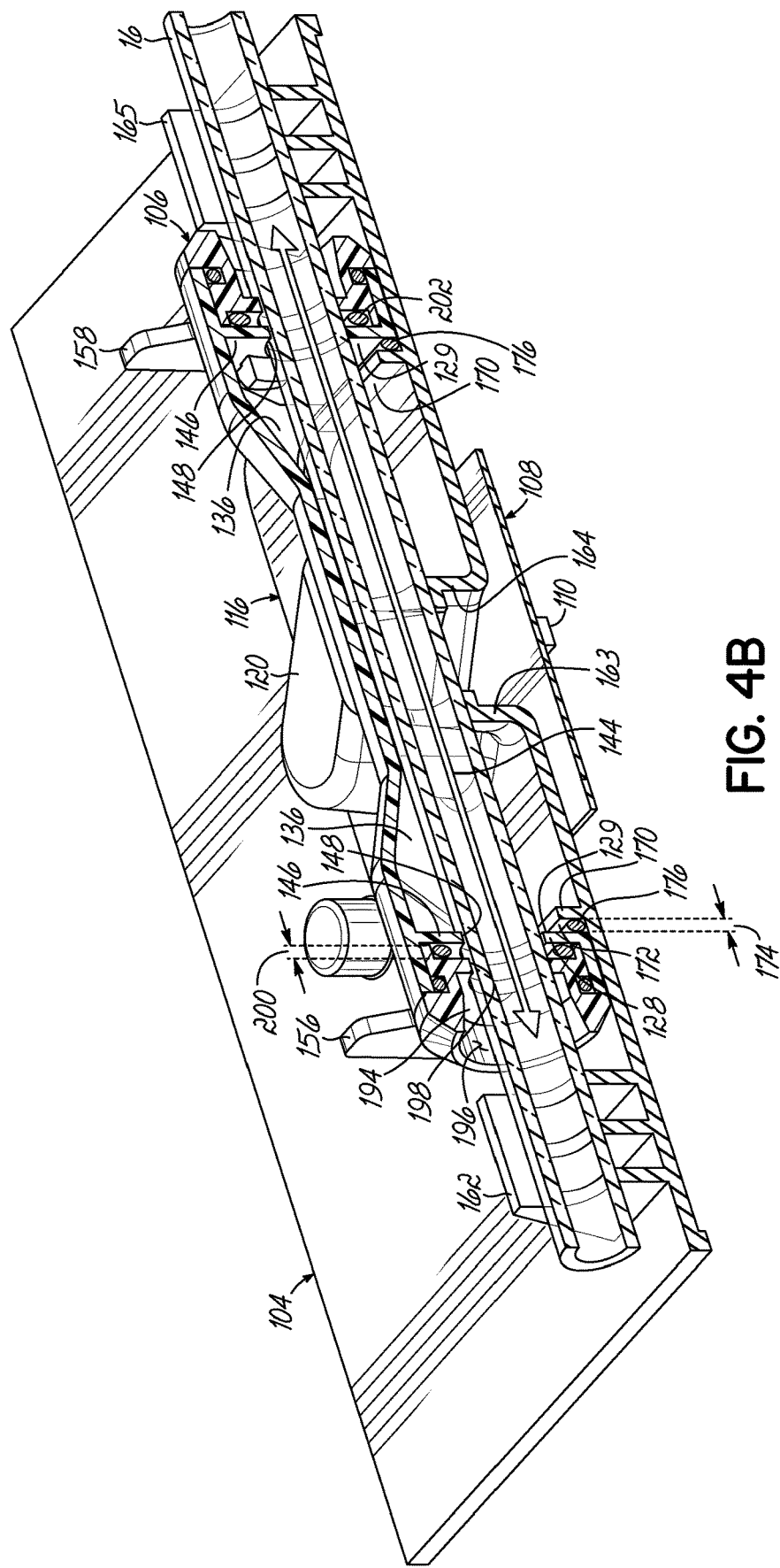
FIG. 4B is a cross-sectional view of the optical sensor assembly of FIG. 4A.
Figure 5A:
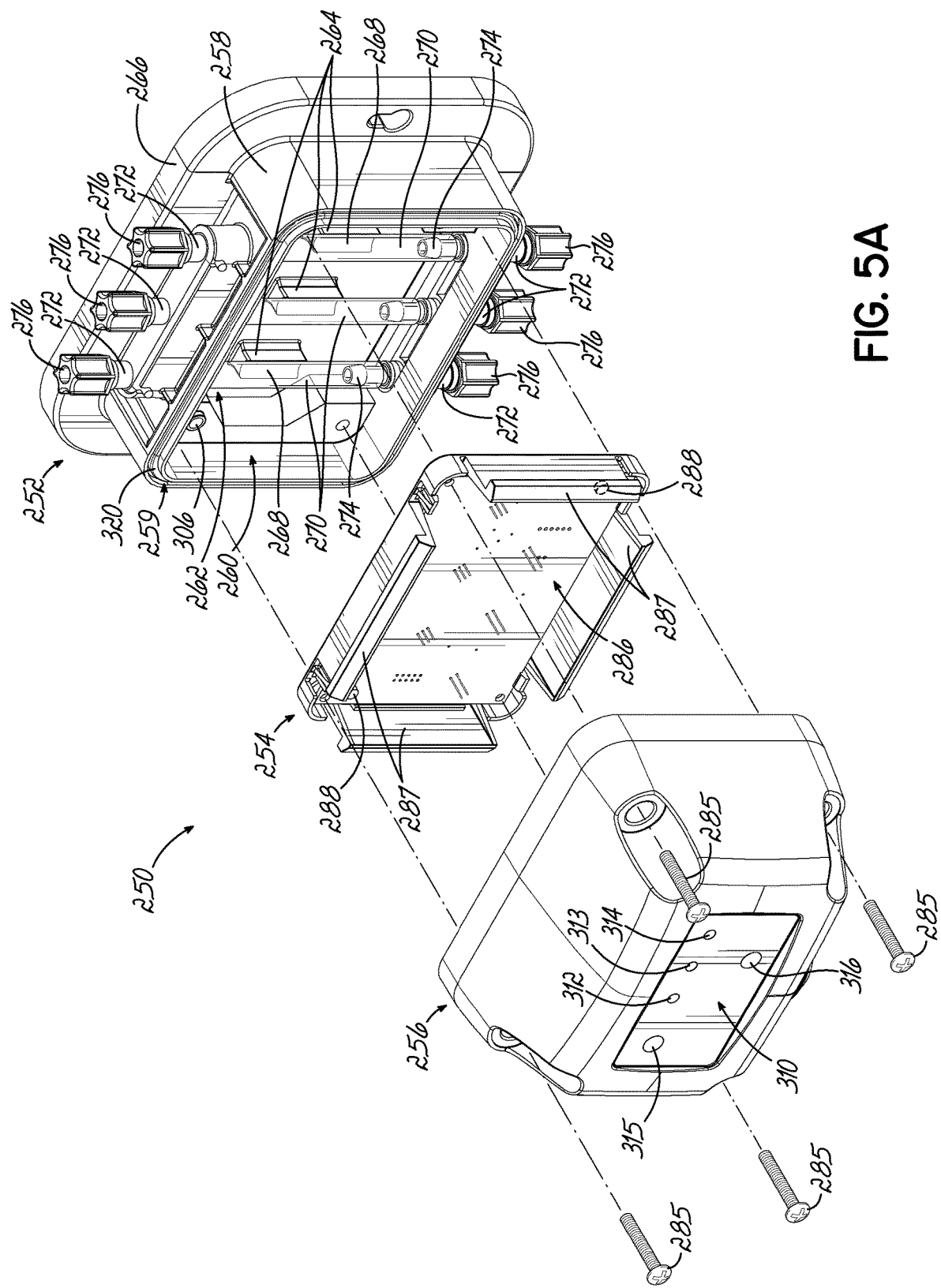
FIG. 5A is an exploded perspective view of an integrated out-of-product detection unit including a plurality of optical sensors each having a guide.
Figure 5B:
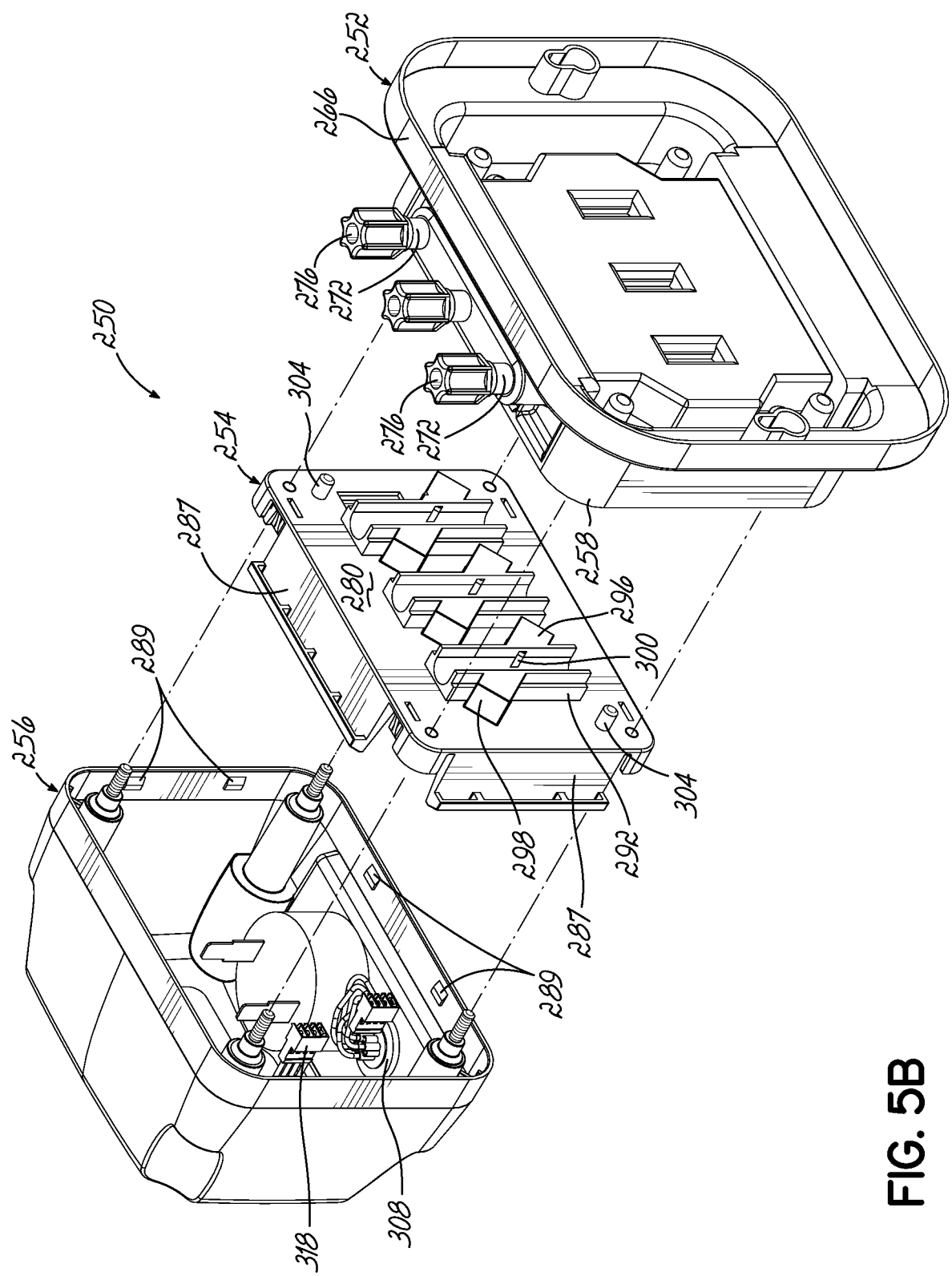
FIG. 5B is an exploded perspective view of the detection unit of FIG. 5A viewed from another angle.
Figures 5C, 5D:
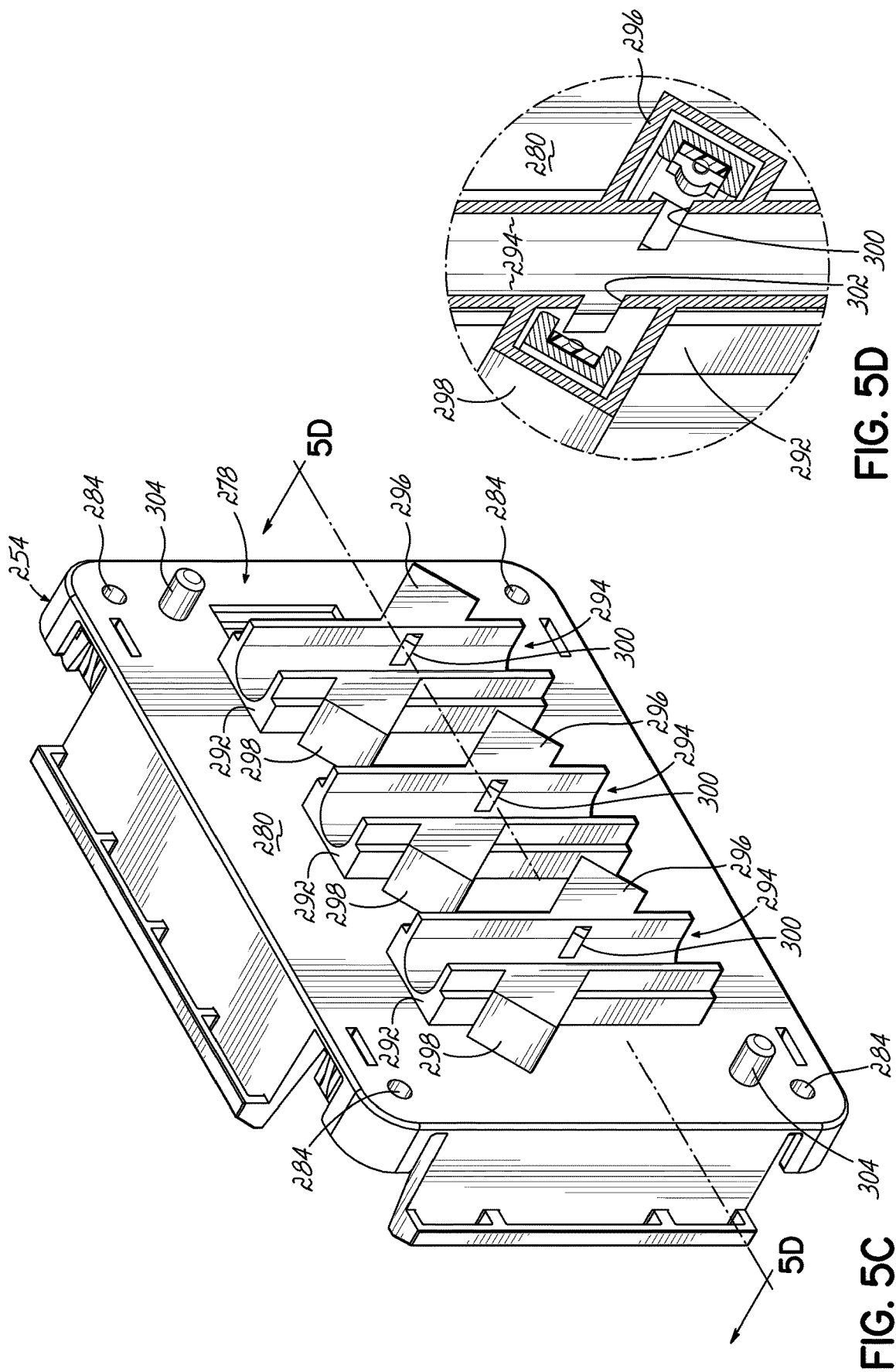
FIG. 5C is a perspective view of the holder of FIGS. 5A and 5B.
FIG. 5D is a cross-sectional view showing additional details of the guides depicted by FIGS. 5B and 5C.

FIGS. 4A and 4B depict a sensor assembly 100 in accordance with an embodiment of the invention that includes a holder 102, a base 104, one or more (e.g., two) caps 106, and a circuit board 108. The circuit board 108 may include a connector 110 configured to electrically couple the circuit board 108 to the detection module 12, a light source 112, and a photodetector 114.

The holder 102 may comprise an elongated body 116 coupled to a rounded rectangular flange 118, and one or more (e.g., two) cavities, the exterior surfaces of which project upward from the flange 118 on opposite sides of body 116 in a staggered arrangement to form sockets 120, 122. The flange 118 may include a generally horizontal portion 124 having an outer circumference 126, and a wall 128. The wall 128 may include an inner surface 129, and may project from the horizontal portion 124 proximal to the circumference 126 in a direction generally away from the body 116 of holder 102.

The body 116 of holder 102 may comprise a center portion 130, cylindrical portions 132, 134 each having an inner opening 136 and an outer opening 138, and generally frustoconical shaped portions 140, 142 that couple the inner openings 136 to the center portion 130. The center portion 130, cylindrical portions 132, 134, and frustoconical shaped portions 140, 142 of body 116 may be axially aligned to define a passage 144 between the outer openings 138 that is configured to receive supply line 16. Each cylindrical portion 132, 134 of body 116 may include an inwardly extending baffle 146 that defines an aperture 148 having a diameter generally equal to or slightly larger than an outer diameter of the supply line 16. The baffle 146 may be longitudinally offset from its corresponding outer opening 138 by a distance sufficient to allow for insertion of the caps 106 into the outer openings 138.

The base 104 may include a horizontal surface 150, one or more hollow adjoined pylons 152, 154, a plurality of retention members 156-159, and a plurality of supports 162-165. Each of the pylons 152, 154, retention members 156-159, and supports 162-165 may project upward from the horizontal surface 150. The pylons 152, 154 may be configured to engage sockets 120, 122 in a nesting relationship. The sockets 120, 122 and pylons 152, 154 may thereby provide alignment elements that positively locate the holder 102 relative to the base 104. An opening 166 may be defined in the adjoined portion of the pylons 152, 154 to provide an optically clear path between, and locate the supply line 16 relative to, the light source 112 and photodetector 114 of circuit board 108.

Retention members 156-159 may be arranged in one or more opposing pairs each providing a snap-fit with the cylindrical portions 132, 134 of body 116. The pairs of retention members 156-159 may thereby retain the holder 102 in a positive engagement with the base 104. The supports 162-165 may collectively define a channel that, when the holder 102 is engaged with the base 104, aligns supply line 16 with the passage 144 between the outer openings 138 of caps 106. To facilitate this alignment, the center portion 130 of holder 102 may act as a guide that urges the supply line 16 into the channel defined by the supports 162-165. A rounded rectangular wall 170 having an outer surface 172 may extend upward from surface 150. The wall 170 may be configured to define a gap 174 between its outer surface 172 and the inner surface 129 of wall 128. An elastic member 176 may be provided in the gap 174 to create a seal between the holder 102 and base 104.

Each cap 106 may include a barrel 178 having an outer surface 180, and a shoulder 182 that extends radially outward from an outer end 184 of cap 106 to form a lip 186. The outer surface 180 of barrel 178 may include a groove 188 proximal to the lip 186. The groove 188 may be configured to receive an elastic ring (not shown) that forms a seal between the cap 106 and the body 116 when an inner end 192 of cap 106 is inserted into the outer opening 138 of the cylindrical portion 134 of body 116. Additional elastic rings (not shown) may provide a seal between the supply line 16 and the cap 106.

A baffle 194 may extend inward from an inner surface 196 of barrel 178 to define an aperture 198 having a diameter generally equal to or slightly greater than the outer diameter of supply line 16. The baffle 194 may be longitudinally offset from the inner end 192 of cap 106 by distance that provides a gap 200 between the baffle 194 of cap 106 and the baffle 146 of the cylindrical portion 132, 134 of body 116. An elastic ring 202 may be positioned in the gap 200 to provide a seal between the holder 104 and the cap 106. The seals between the supply line 16, holder 102, base 104, and cap 106 of sensor assembly 100 provided by the elastic rings/members may prevent product from entering the sensor assembly 100 in the event of a leak and impairing operation of the optical sensor 14.

FIGS. 5A-5D depict a detection unit 250 that integrates the detection module 12 and one or more optical sensors 14 in accordance with an embodiment of the invention. The detection unit 250 includes a base 252, a holder 254, and a cover 256. The base 252 may include a generally rectangular sidewall 258 having a channel 259 at the top thereof that defines the perimeter of an opening 260, a back wall 262 opposite the opening 260 from which one or more (e.g., three) supports 264 project toward the opening 260, and a flange 266 that projects laterally away from the sidewall 258. Each support 264 may include a channel 268 at a distal end thereof. The channel 268 may be configured to receive and locate a connecting tube 270 relative to the base 252. To this end, the channel 268 may have a radius of curvature generally equal to the radius of the outer diameter of connecting tube 270.

A plurality of through-hole fluidic couplers 272 may be arranged in sidewall 258 in one or more pairs such that the fluidic couplers 272 of each pair are mounted in opposing sides of sidewall 258. Each fluidic coupler 272 may be configured to securely couple an end of a corresponding supply line 16 to the detection unit 250. To this end, each fluidic coupler 272 may include an inner connector 274 that projects inward from sidewall 258 and an outer connector 276 that projects outward from sidewall 258. The outer connector 276 may include, for example, a threaded coupling configured to receive an end of the supply line 16. The inner connector 274 may be a push-on connector comprising a nozzle configured to receive an end of the connecting tube 270. The inner connector 274 may further include one or more barbs or serrations that prevent the end of the connecting tube 270 from slipping off the inner connector 274.

The inner connectors 274 of each pair of couplers may be aligned along a direction of flow so that the connecting tube 270 coupling the inner connectors 274 traverses the base 252 along a path that passes through the channel 268 of a corresponding support 264. For embodiments including more than one pair of fluidic couplers 272, the pairs of couplers may be configured so that the corresponding connecting tubes 270 are generally parallel to the other connecting tubes 270 of the detection unit 250.

Holder 254 may include a panel 278 having a base facing side 280, a cover facing side (not visible) opposite the base facing side 280, one or more openings 284 each configured to allow passage of a fastener 285, and one or more retention members 287 configured to provide a snap-fit with a corresponding set of catches 289 on the interior surface of cover 256. The cover facing side may be configured to receive a circuit board 286. The circuit board 286 may include a light source and at least one photodetector for each connecting tube 270 of base 252, as well as the processor 34, memory 36, and I/O interface 38 of detection module 12. One or more alignment elements 288 (e.g., columns) may extend outward from the cover facing side of panel 278. The alignment elements 288 may be configured to engage one or more matching alignment elements 290 (e.g., openings) in the circuit board 286. The alignment elements 288, 290 may thereby locate the circuit board 286 laterally relative to the panel 278.

The base facing side 280 of panel 278 may include one or more guides 292 (e.g., three guides) each including a semi-cylindrical channel 294. Each guide 292 may be configured to urge a respective connecting tube 270 into engagement with the channel 268 of a corresponding support 264 when the holder 254 is coupled to base 252. In an embodiment of the invention, the channels 268, 294 may be configured to compress the connecting tubes 270 into an oval or elliptical shape when the fasteners 285 holding together the detection unit 250 are tightened. This compression may flatten the outer surface of the connecting tubes 270 at the points of incidence 66, 88 of beam of light 62. The flattening of the connecting tubes 270 may improve transmittance through the optical path by reducing the amount of the beam of light 62 reflected away from the optical path at the points of incidence 66, 88.

Each guide 292 may be straddled by diagonally aligned chambers 296, 298. Each of the chambers 296, 298 may be configured to enclose a respective one of the light source or photodetector of circuit board 286. Each guide 292 and its respective chamber 296, 298 may be formed (e.g., molded) in the panel 278. The diagonally aligned chambers 296, 298 may each include a respective aperture 300 configured to provide an optical path between a corresponding light source and photodetector pair when the circuit board 286 is mounted to the cover facing side of panel 278.

The holder 254 may further include one or more alignment elements 304 (e.g., cylindrical columns) that project outward from the base facing side 280 of panel 278. Each of the alignment elements 304 may be configured to interface with a corresponding alignment element 306 (e.g., another cylindrical column) that projects outward from the back wall 262 of base 252. The alignment elements 304, 306 may be configured to locate the base 252 relative to the holder 254, and may work cooperatively with the supports 264, alignment elements 288, 290, and guides 292 to maintain the light sources, photodetectors, and connecting tubes 270 in predetermined positions relative to each other.

The cover 256 may include a connector 308 through which the circuit board 286 receives power, and a display panel 310. The display panel 310 may include one or more (e.g., three) indicators 312-314 and one or more input devices 315, 316 (e.g., an enable button and a mute button) for controlling operation of the detection module 12. The indicators 312-314 and input devices 315, 316 may be coupled to the circuit board 286 through another connector 318. The indicators 312-314 may be selectively activated and deactivated by the detection module 12 to provide an indication to the user of whether an out-of-product condition has been detected and/or information regarding operation of the detection module 12. The cover 256 may be configured so that when the detection unit 250 is assembled, the cover 256 engages an elastic member 320 in channel 259 of sidewall 258 to provide a fluid-tight seal between the base 252 and cover 256.

The detection module 12 may be configured to enter a standby mode when initially powered up. The detection module 12 may remain in the standby mode until the user activates the detection module 12, e.g., by activating an input device such as the enable button. In response to the user activating the detection module 12, the detection module 12 may begin a start-up process by sequentially activating each of the optical sensors 14. The start-up process may begin with all the supply lines 16 in a dry state, i.e., when no products or other liquids are in the supply lines 16. To select which supply lines 16 will be monitored by the detection module 12, the user may press and hold one or more input devices (e.g. the enable and mute buttons) for a period of time (e.g., 5 seconds) to enter a programming mode. While in the programming mode, the detection module 12 may allow the user to selectively sequence through each detector input, with one detector input being a default starting position.

In response to activation of an input device (e.g., the enable button), the detection module 12 may sequentially activate programming of each detector input. While programming is activated for an input, activation of an input device (e.g., the mute button) may cause the detection module 12 to toggle the selected detector input between active and inactive modes. When the user is finished selecting which detector inputs will be active and which will be inactive, the user may exit the programming mode by pressing and holding one or more input devices (e.g., the enable and mute buttons) for a period of time (e.g., 5 seconds). If the user fails to exit the programming mode correctly, the detection module 12 may abort the setup and return to its previous or default settings.

For each optical sensor 14, the detection module 12 may receive and store a voltage level received from the optical sensor 14 in memory as a baseline value. This baseline value may be a voltage associated with a supply line 16 in a dry state, and may be used by the detection module 12 to determine an out-of-product criteria. To guard against improper start-up conditions (e.g., a start-up while the supply lines 16 are filled with product), the detection module 12 may validate the voltage received from each optical sensor 14 during the start-up process. For example, a voltage may only be considered valid if it falls with a predetermined voltage window having an upper and lower limit over a plurality of (e.g., 16) sample periods.

Upon power-up, the detection module 12 may signal the beginning of the start-up mode, e.g., by illuminating all indicators 312-314 simultaneously for a period of time (e.g., 1 second) and then returning them to an off state. When the detection module 12 completes the dry state voltage sampling process for an optical sensor 14, the detection module 12 may provide an indication of this by, for example, causing the indicator 312-314 associated with that optical sensor 14 to blink a number of times, e.g., two times. This may allow the user to determine when the dry state voltage sampling process has been completed for each of the optical sensors 14.

When the detection module 12 has completed the dry state voltage sampling process, the user may flood each supply line 16. The user may then provide an indication to the detection module 12 that the supply lines 16 have been flooded by activating an input device, e.g., pressing the enable button. In response, the detection module 12 may sample the voltage present on each detector input the user has activated to obtain a wet state voltage for each optical sensor 14. This sampling may be performed in a similar manner as described above with respect to the dry state voltage sampling process. If the wet state voltage is more than a predetermined amount (e.g., 200%) greater than the dry state voltage for a detector input, the detection module 12 may determine that the supply line 16 associated with that detector input is functioning, and enable the indicator associated with that detector input to indicate the associated supply line 16 is now active and being monitored. The detection module 12 may repeat the above wet state voltage validation process for each activated detector input that has a valid dry state voltage value stored in memory.

Once setup is complete, the detection module 12 may cause the indicators 312-314 associated with active detector inputs (i.e., the inputs that are being used to monitor respective supply lines 16) to be illuminated, and the indicators 312-314 associated with inactive detector inputs (i.e., the inputs that are not being used to monitor respective supply lines 16) to be unilluminated. The indicators 312-314 may thereby be used by the detection module 12 to indicate which detector inputs are active.

In response to determining that one of the active optical sensors 14 is providing a signal indicative of an out-of-product condition, the detection module 12 may cause the associated indicator indicate this condition, e.g., by blinking on and off. Thus, a blinking indicator 312-314 may indicate an out-of-product condition (or some other error) on the associated supply line 16. The detection module 12 may return the indicator 312-314 to the normal mode (e.g., constantly lit) once the out-of-product condition or other error has been rectified, and product is once again detected in the supply line 16.

As product begins to run out, it may be replaced with columns of air in portions of the supply line 16. These columns of air may change the refractive index n of the material in the supply line 16. This change in the refractive index n may alter the characteristics of the optical path(s) between the light source and photodetector(s) of the optical sensor 14. This change in the characteristics of the optical path may affect the intensity of the light at one or more photodetectors by bending the beam of light 62 towards or away from the respective aperture coupling the beam of light 62 to the photodetector. Pockets of air in the supply line 16 may thereby cause the beam of light 62 to be directed towards (or away) from the respective aperture. The resulting change in the intensity of the light detected by the photodetector may provide an indication of an out-of-product condition to the detection module 12.

A monitoring application in the detection module 12 may cause the detection module 12 to periodically activate each light source 52 for a predetermined period of time. Periodic activation of the light source 52 may reduce power consumption as compared to constant activation. This feature may be particularly advantageous for embodiments of the invention that are powered by batteries.

The detection module 12 may determine the intensity of the light at each photodetector being monitored, and compare this intensity to an expected intensity. The expected intensities for normal operation and an out-of-product condition may depend on whether the optical sensor 14 is configured to direct the beam of light 62 toward or away from the photodetector in the presence or absence of product in the supply line 16. Based on this comparison, the detection module 12 may determine if the product is running out. In response to detecting an out-of-product condition, the detection module 12 may alert the user. This determination may be triggered by an absence of product in the tubing between the light source and the one or more photodetectors of the optical sensor 14.

To enhance the alert mode, the detection module 12 may be configured to provide different audio and/or visual indicators as the out-of-product event continues. For embodiments having a mute button, activation of the mute button may implement a mute feature that silences the audible indicator for a predetermined amount of time. In cases where the detection module 12 detects a new out-of-product condition (e.g., in another monitored supply line 16) while muted, the detection module 12 may reactivate the audible indicator.

In an embodiment of the invention, pressing the mute button for a predetermined period of time (e.g., 2 seconds) may cause the detection module 12 to mute the audible indicator for one predetermined muting period (e.g., 15-minutes). Pressing the mute button for another period of time (e.g., 5 seconds) may cause the detection module 12 to mute the audible indicator for a different predetermined muting period (e.g., 24 hours). In either case, the detection module 12 may alter the output of the indicators 312-314 (e.g., rate at which the indicators 312-314 are blinked on and off) to indicate that the detection module 12 is muted. Once the depleted product has been replenished, the detection module 12 may detect the presence of product in the supply line 16. If the detection module 12 detects product in the supply line 16 for a predetermined amount of time, it may cancel the alarm condition without any user intervention being required.

The detection module 12 may also notify the controller 30 of product status. This notification may be transmitted, for example, through a power or data cable to an unused optical trigger port on the controller 30. The detection module 12 may use any suitable transmission protocol to transfer data to the controller 30, such as a proprietary one way protocol, so that the controller 30 can log status changes in its memory. The detection module 12 may provide packetized serial data to any off-board device that relates to the operational information that is being collected. The off-board device may in turn provide this data to other devices using any suitable communication channel, such as a wired, wireless, or power line communication channel.

The detection module 12 may execute a detection algorithm that determines when an out-of-product condition exists based on detected changes in the intensity of light at one or more photodetectors. The intensity of light incident on a photodetector may be indicated by a voltage level output by the photodetector. The detection module 12 may detect a significant change in the voltage received from a photodetector due to the beam of light 62 being shifted toward or away from the aperture coupling the light to the photodetector. In the case of bubbles of air being introduced in the supply line 16 (e.g., when the product is beginning to run low), the beam of light 62 may be diffused, which may also affect the intensity of the light at the photodetectors 54, 56. Using these changes in voltage, the detection module 12 may determine that a product is running low based on an absence of the product in the supply line 16, and alert the user.

The detection module 12 may sample the voltage provided by the photodetector over time and detect changes in the voltage between samples. In response to detecting a change in voltage that breaches a threshold (e.g., the voltage drops below a predetermined value), the detection module 12 may increment a counter associated with the optical sensor 14 providing the voltage. This counter may maintain a running count of a number of detection events, e.g., the number of times the voltage has dropped below the predetermined value. This predetermined value may be determined by the detection module 12 based on voltage levels that were detected and stored in memory while the supply line 16 was known to be free of product, i.e., during system initialization before the supply lines 16 were flooded.

If the number of detection events exceeds a threshold within a predetermined period of time, the detection module 12 may determine that an out-of-product condition exists for the product in question. Requiring a predetermined number of detection events to occur within a predetermined period of time may provide a smoothing effect so that random pockets of air (e.g., due to a poorly manufactured cap or connection to the source of product 18) do not trigger false out-of-product alarms. If detection events occur but do not meet the requirements of the out-of-product condition in either number or frequency, the detection module 12 may generate an alarm that is distinguishable from an out-of-product alarm (e.g., having a different audible tone) to inform the user there may be a "leaky" system. In some applications, leaks may cause pumps that provide the product to the machine 20 to lose prime over time, and therefore should be addressed by the user to prevent system failure.

Figure 6:
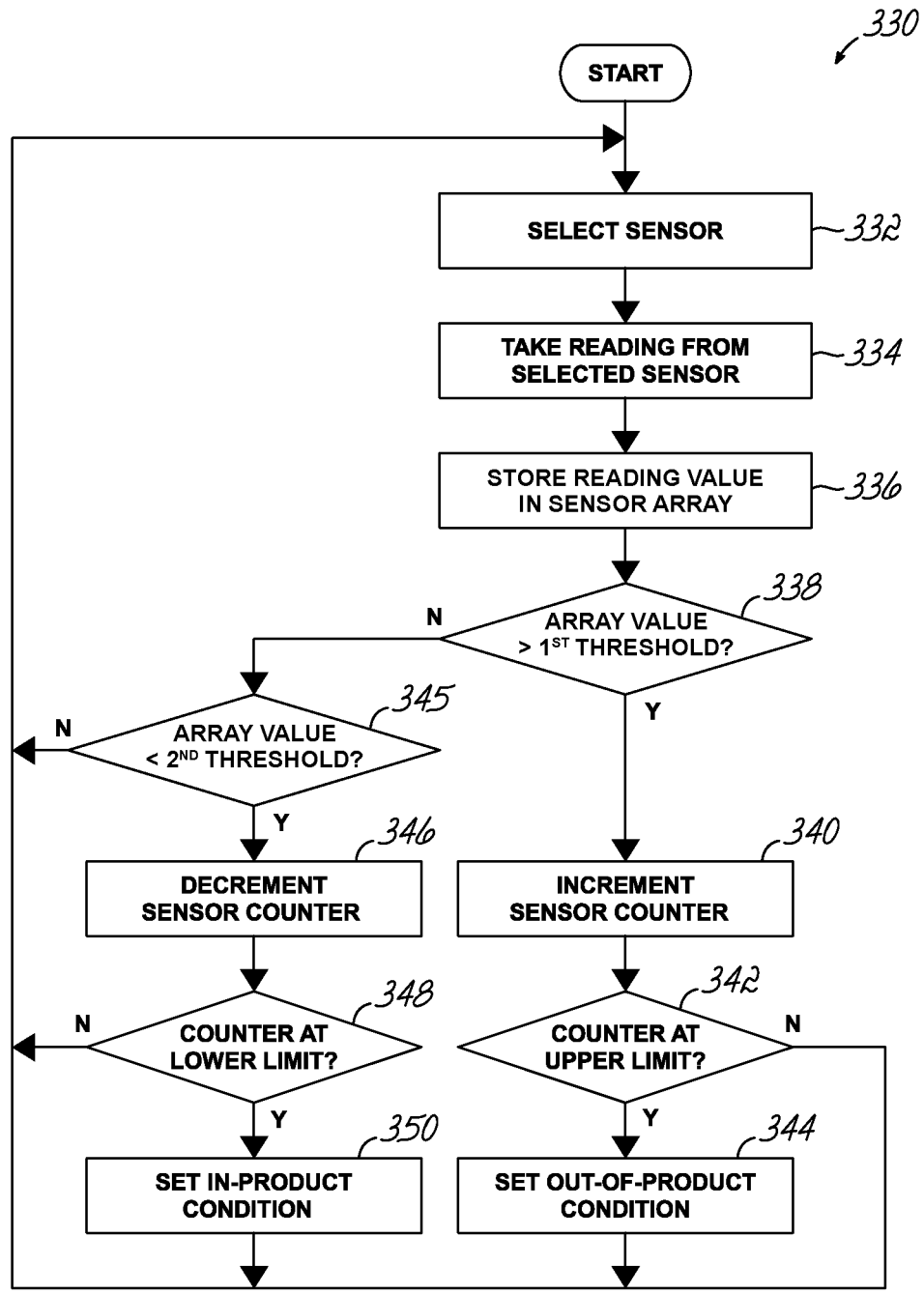
FIG. 6 depicts a flow chart illustrating a process for detecting in-product and out-of-product conditions based on signals from the optical sensor of FIG. 1.

FIG. 6 presents a flowchart depicting an exemplary process 330 that may be executed by the detection module 12 to detect in-product and out-of-product conditions based on signals from the optical sensors 14. In block 332, the process 330 may select an optical sensor 14 to read. The sensor selected may be the next sensor in a repeating sequence of sensors being monitored by the detection module 12. The process 330 may select the sensor, for example, by causing the I/O interface 38 to couple the selected optical sensor 14 to the processor 34. The process 330 may also retrieve an array and a counter associated with the selected optical sensor 14, e.g., from memory 36.

In response to selecting the optical sensor 14, the process 330 may proceed to block 334 and take a reading from the selected sensor. Taking the reading may include activating the light source 52 of the selected optical sensor 14. The process 330 may activate the light source 52, for example, by causing the I/O interface 38 to provide a suitable signal (e.g., voltage or current) to the optical sensor 14. This signal may be provided to the light source 52 of the selected sensor for a predetermined amount of time, e.g., 270 µs.

While the light source 52 is activated, the process 330 may sample the output of one or more of the photodetectors 54, 56. Sampling may include receiving an electrical signal from a photodetector 54, 56 of the optical sensor 14 and converting a voltage of the signal to a digital value using an A/D converter. The process 330 may proceed to block 336 and store the reading in the array associated with the selected sensor. The array may include a predetermined number of elements (e.g., 16 elements), with each element representing a reading obtained from the selected sensor. The process 330 may store the reading in the array by replacing the oldest element in the array with the most recent reading to maintain a fixed number of elements in the array. That is, the process 330 may use a First In, First Out (FIFO) strategy for storing readings in the array.

In block 338, the process 330 may determine if a value of the array has breached a threshold. This determination may include, for example, determining an average value of the elements in the array, and comparing this average value to the threshold. The threshold may be, for example, a value representing a voltage received from the photodetector 54, 56, e.g., one volt. If the value of the array has breached the threshold ("YES" branch of decision block 338), the process 330 may proceed to block 340 and increment the counter associated with the selected sensor. The process 330 may then proceed to block 342 and determine the condition of the source of product 18 associated with the selected sensor based on the value of the counter.

In block 342, the process 330 may determine if the counter has reached an upper limit. The upper limit may be determined based on a rate at which the selected sensor is sampled so that the upper limit corresponds to an amount of time that the selected sensor has been in breach of the threshold, e.g., 12 seconds. If the counter has not reached the upper limit ("NO" branch of decision block 342), the process 330 may return to block 332 and select the next sensor in the monitoring sequence. If the value of the counter has reached the upper limit ("YES" branch of decision block 342), the process 330 may proceed to block 344.

In block 344, the process 330 may set the condition of the source of product 18 associated with the selected sensor to an out-of-product, or "OOP", condition. Concurrently with setting the OOP condition of the source of product 18, the process 330 may also set the value of the counter to a predetermined value that provides a level of hysteresis for the OOP condition. For example, for an upper limit corresponding to 12 seconds, the process may set the value of the counter to correspond to 16 seconds. The process 330 may then return to block 332 and select the next sensor in the monitoring sequence.

If the process 330 determines the value of the array has not breached the threshold ("NO" branch of decision block 338), the process 330 may proceed to block 345 and determine if the value of the array has breached a second threshold. If the value of the array has breached the second threshold ("YES" branch of decision block 345), the process 330 may proceed to block 346 and decrement the counter associated with the selected sensor. The process 330 may then proceed to block 348 and determine the condition of the source of product 18 associated with the selected sensor based on the value of the counter.

In block 348, the process 330 may determine if the counter has reached a lower limit, e.g., zero. If the counter has not reached the lower limit ("NO" branch of decision block 348), the process 330 may return to block 332 and select the next sensor in the monitoring sequence. If the value of the counter has reached the lower limit ("YES" branch of decision block 348), the process 330 may proceed to block 350. In block 350, the process 330 may set the condition of the source of product 18 associated with the selected sensor to an in-product condition. The process 330 may then return to block 332 and select the next sensor in the monitoring sequence.

The process 330 may be configured so that the value of the array of each sensor is checked regularly, e.g., once every 400 ms. In this case, the amount of time associated with a counter value may be the value of the counter k times the array checking period, e.g., k×0.4 sec. The process 330 may also be configured so that the optical sensors 14 are read regularly, e.g., once every 12.5 ms. The detection scheme implemented by process 330 may essentially comprise maintaining a running count of how often the average value of the elements in each sensor array is above or below the threshold.

The underlying concept of the detection process may be that pulses having a value above/below a threshold are counted (by incrementing or decrementing the counter) to determine, with a high level of accuracy, whether the supply line 16 associated with the sensor in question is in a dry state. If the count reaches the upper limit within a predetermined amount of time (e.g., the array has an average value indicative of the dry state for 12 consecutive seconds), the counter may be set to a value corresponding to a predetermined period of time (e.g., 16 seconds) that provides a level of stability to the system. A wet state may then have to be detected for the predetermined period of time before the out-of-product condition is cleared and an in-product condition set. That is, the counter may have to be decremented back to the lower limit (e.g., zero) from the augmented level (e.g., 16 seconds) before the in-product condition is set, and may be reset to the augmented level (e.g., 16 seconds) each time the dry state is detected based on the value of the array.

It has been determined that increasing the angle of incidence 70 of beam of light 62 may result in a corresponding increase in the separation between the angle of emittance 78 of the supply line 16 in a dry state and the angle of emittance 78 of the supply line 16 in a wet state. Thus, a relatively larger angle of incidence (e.g., 70 degrees) may provide a greater separation than a relatively smaller angle of incidence (e.g., 45 degrees). By way of example, an optical sensor 14 configured to have a 70-degree angle of incidence may have a separation between the angles of emittance 78 of supply lines 16 in dry and wet states of over 15 degrees. Having a greater separation between the angles of emittance may facilitate certain methods of detecting an out-of-product condition.

For example, rather than using a 100% duty cycle when activating the light source, the detection module 12 may transmit a plurality of electrical pulses to the light source. The detection module 12 may then count the number of pulses received from the photodetector to determine if the supply line 16 is in a wet state or a dry state. Greater separation may also enable the aperture coupling the refracted beam of light to the photodetector to be placed farther away from the expected exit angle, thereby reducing the intensity of the light being received by the photodetector when product is not present in the supply line 16.

This increased sensitivity may enable embodiments of the invention using large angles of incidence to operate without obtaining a baseline value for the output of the optical sensors 14 when the supply line 16 is in a dry state, and may enable detection of out-of-product conditions without using voltage threshold values. That is, rather than comparing voltages received from the optical sensors 14 to threshold values, the detection module 12 may determine one condition is present (e.g., the supply line 16 is in a wet state) if pulses from the optical sensor are detected, and another condition is present (e.g., an out-of-product condition) if pulses are not detected.

In certain embodiments, the detection module 12 and/or optical sensors 14 may be integrated into a pumpstand or other type of pumping dispenser. In these embodiments, the optical sensors 14 may be implemented as an extension of a product input port ahead of a squeeze tube assembly of a peristaltic pump. A controller for the pumpstand could be configured to handle all of the processing and reporting functions, and the supply line 16 monitored by the optical sensors 14 could be an elongated section of a standard squeeze tube. In addition, although the optical sensors 14 are depicted as being coupled to supply lines 16, optical sensors 14 may also be coupled to the machine supply line 24. In this case, the detection module 12 and sensors may be configured to determine whether there is an out-of-product condition in one of the supply lines 16 based on changes to the refractive index of the solution being provided to the machine 20 through the machine supply line 24.

In general, the routines executed to implement the embodiments of the invention, whether implemented as part of an operating system or a specific application, component, program, object, module or sequence of instructions, or a subset thereof, may be referred to herein as "computer program code," or simply "program code." Program code typically comprises computer-readable instructions that are resident at various times in various memory and storage devices in a computer and that, when read and executed by one or more processors in a computer, cause that computer to perform the operations necessary to execute operations and/or elements embodying the various aspects of the embodiments of the invention. Computer-readable program instructions for carrying out operations of the embodiments of the invention may be, for example, assembly language or either source code or object code written in any combination of one or more programming languages.

Various program code described herein may be identified based upon the application within which it is implemented in specific embodiments of the invention. However, it should be appreciated that any particular program nomenclature which follows is used merely for convenience, and thus the invention should not be limited to use solely in any specific application identified and/or implied by such nomenclature.

Furthermore, given the generally endless number of manners in which computer programs may be organized into routines, procedures, methods, modules, objects, and the like, as well as the various manners in which program functionality may be allocated among various software layers that are resident within a typical computer (e.g., operating systems, libraries, API's, applications, applets, etc.), it should be appreciated that the embodiments of the invention are not limited to the specific organization and allocation of program functionality described herein.

The program code embodied in any of the applications/modules described herein is capable of being individually or collectively distributed as a program product in a variety of different forms. In particular, the program code may be distributed using a computer-readable storage medium having computer-readable program instructions thereon for causing a processor to carry out aspects of the embodiments of the invention.

Computer-readable storage media, which is inherently non-transitory, may include volatile and non-volatile, and removable and non-removable tangible media implemented in any method or technology for storage of data, such as computer-readable instructions, data structures, program modules, or other data. Computer-readable storage media may further include RAM, ROM, erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store the desired data and which can be read by a computer. A computer-readable storage medium should not be construed as transitory signals per se (e.g., radio waves or other propagating electromagnetic waves, electromagnetic waves propagating through a transmission media such as a waveguide, or electrical signals transmitted through a wire). Computer-readable program instructions may be downloaded to a computer, another type of programmable data processing apparatus, or another device from a computer-readable storage medium or to an external computer or external storage device via a network.

Computer-readable program instructions stored in a computer-readable medium may be used to direct a computer, other types of programmable data processing apparatuses, or other devices to function in a particular manner, such that the instructions stored in the computer-readable medium produce an article of manufacture including instructions that implement the functions, acts, and/or operations specified in the flow-charts, sequence diagrams, and/or block diagrams. The computer program instructions may be provided to one or more processors of a general purpose computer, a special purpose computer, or other programmable data processing apparatus to produce a machine, such that the instructions, which execute via the one or more processors, cause a series of computations to be performed to implement the functions, acts, and/or operations specified in the flow-charts, sequence diagrams, and/or block diagrams.

In certain alternative embodiments, the functions, acts, and/or operations specified in the flow-charts, sequence diagrams, and/or block diagrams may be re-ordered, processed serially, and/or processed concurrently consistent with embodiments of the invention. Moreover, any of the flow-charts, sequence diagrams, and/or block diagrams may include more or fewer blocks than those illustrated consistent with embodiments of the invention.

The terminology used herein is for the purpose of describing particular embodiments only and is not intended to be limiting of the embodiments of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, actions, steps, operations, elements, and/or components, but do not preclude the presence or addition of one or more other features, integers, actions, steps, operations, elements, components, and/or groups thereof. Furthermore, to the extent that the terms "includes", "having", "has", "with", "comprised of", or variants thereof are used in either the detailed description or the claims, such terms are intended to be inclusive in a manner similar to the term "comprising".

While all the invention has been illustrated by a description of various embodiments, and while these embodiments have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicant's general inventive concept.

What is claimed is:

1. An apparatus for monitoring a chemical dispensing system, comprising:
 a first photodetector;
 a light source configured to generate a beam of light;
 a holder configured to position the light source and the first photodetector relative to a tube that carries a product such that the beam of light has an oblique angle of incidence with respect to an outer surface of the tube, and the first photodetector is in an optical path of the beam of light when the tube is in one of a dry state or a wet state, and is not in the optical path of the beam of light when the tube is in the other of the dry state or the wet state;
 a processor; and
 a memory coupled to the processor and containing program code that, when executed by the processor, causes the processor to:
 sample a first signal generated by the first photodetector;
 generate a reading value characterizing the sample;
 store the reading value in the memory as an element in an array having a plurality of elements each corresponding to a previously stored reading value;
 generate an array value based on the plurality of elements in the array; and
 if the array value is greater than a first threshold, increment a counter;
 if the array value is less than a second threshold, decrement the counter;
 and determine whether an out-of-product condition exists based on the counter.

2. The apparatus of claim 1 wherein the program code further causes the processor to:
 compare a value of the counter to an upper limit; and
 if the value of the counter is at the upper limit, set the out-of-product condition.

3. The apparatus of claim 1, further comprising:
a second photodetector,
wherein the holder is further configured to position each of the first photodetector and the second photodetector relative to the tube that carries the product such that the first photodetector is in an optical path of the beam of light when the tube is in a wet state, and is not in the optical path of the beam of light when the tube is in a dry state and the second photodetector is in the optical path of the beam of light when the tube is in the dry state.

4. The apparatus of claim 3, wherein:
the memory when further executed by the processor, causes the processor to:
receive a second signal from the second photodetector;
compare the first signal and the second signal; and
determine if the tube is in the wet state or the dry state based on the comparison.

5. The apparatus of claim 3 wherein the holder includes a guide, and further comprising:
a base including a support configured to operate in cooperation with the guide to position the tube in a fixed position relative to the holder.

6. The apparatus of claim 5 wherein the holder includes a first alignment element and the base includes a second alignment element configured to engage the first alignment element, the engagement of the first and second alignment elements positioning the holder in a fixed position relative to the base.

7. An apparatus for monitoring a chemical dispensing system, comprising:
a photodetector;
a light source configured to generate a beam of light;
a holder configured to position the light source and the photodetector relative to a tube that carries a product such that the beam of light has an oblique angle of incidence with respect to an outer surface of the tube, and the photodetector is in an optical path of the beam of light when the tube is in one of a dry state or a wet state, and is not in the optical path of the beam of light when the tube is in the other of the dry state or the wet state;
a processor; and
a memory coupled to the processor and containing program code that, when executed by the processor, causes the processor to:
activate the light source using a plurality of electrical pulses;
count pulses received from the photodetector; and
determine if the tube is in the wet state or the dry state based on a number of pulses counted.

* * * * *